US 8,045,680 B2

(12) United States Patent
Taoka et al.

(10) Patent No.: US 8,045,680 B2
(45) Date of Patent: Oct. 25, 2011

(54) IMAGING DEVICE (75) Inventors: Akira Taoka, Hamamatsu (JP);
Kazuhisa Miyaguchi, Hamamatsu (JP)

(73) Assignee: Hamamatsu Photonics K.K.,
Hamamatsu-shi, Shizuoka (JP)

( * ) Notice: Subject to any disclaimer, the term of this patent is extended or adjusted under 35 U.S.C. 154(b) by 82 days.

(21) Appl. No.: 12/515,851

(22) PCT Filed: Nov. 19, 2007

(86) PCT No.: PCT/JP2007/072391
§ 371 (c)(1),
(2), (4) Date: Jun. 11, 2009

(87) PCT Pub. No.: WO2008/062756
PCT Pub. Date: May 29, 2008

(65) Prior Publication Data
US 2010/0054405 A1    Mar. 4, 2010

(30) Foreign Application Priority Data
Nov. 22, 2006 (JP) ................. 2006-316052

(51) Int. Cl.
*H05G 1/56* (2006.01)

(52) U.S. Cl. .................................................. 378/114
(58) Field of Classification Search .................. 378/62, 378/114–116
See application file for complete search history.

(56) References Cited

U.S. PATENT DOCUMENTS
2005/0078793 A1*  4/2005  Ikeda .......................... 378/98.8

FOREIGN PATENT DOCUMENTS
| CN | 1610521 | 4/2005 |
|----|---------|--------|
| JP | 6-507796 | 9/1994 |
| JP | 7-270136 | 10/1995 |
| JP | 3335350 | 8/2002 |
| JP | 2005-287773 | 10/2005 |

* cited by examiner

*Primary Examiner* — Courtney Thomas
(74) *Attorney, Agent, or Firm* — Drinker Biddle & Reath LLP

(57) ABSTRACT

An imaging device includes an imager 7 which images an X-ray image generated by X-ray irradiation; an X-ray detector 90 which detects X-ray irradiation and outputs a detected signal showing the result of the detection; an EP-ROM 93a storing an offset value of the X-ray detector 90; and a signal processor 61 which generates reference information for acquiring a start timing of imaging by the imager 7 from the detected signal based on the offset value stored in the EP-ROM 93a.

4 Claims, 7 Drawing Sheets

Fig.7

IMAGING DEVICE

TECHNICAL FIELD

The present invention relates to an imaging device which images an X-ray image.

BACKGROUND ART

Patent Document 1 listed below discloses an X-ray imaging device (X-ray image forming apparatus) which images an X-ray image of teeth, etc., of an examinee by using an image sensor including a CCD (Charge Coupled Devices). This image sensor includes, in addition to the CCD for imaging an X-ray image, a monitoring photodiode (X-ray detector) for detecting an X-ray irradiation timing. Based on an output signal from the X-ray detector, a trigger signal showing the start or the end of X-ray imaging is generated. In detail, when the value of the output signal exceeds a predetermined threshold, a trigger signal showing the start of X-ray imaging is generated.

Patent Document 1: Japanese Published Examined Patent Application No. 3335350

DISCLOSURE OF THE INVENTION

Problem to be Solved by the Invention

However, an offset value of the output signal from the X-ray detector is different among X-ray detectors, and even in the case where the X-ray intensity is the same, if the X-ray detector is different, the value of the output signal is also different. Therefore, there is a possibility that even when an X-ray is irradiated, the value of the output signal does not exceed a preset threshold and a trigger signal showing the start of X-ray imaging is not generated. Therefore, an object of the present invention is to provide an imaging device which can accurately generate a trigger showing the start of X-ray imaging according to the offset value of the X-ray detector.

Means for Solving the Problem

An imaging device of the present invention includes an imager which images an X-ray image generated by X-ray irradiation; an X-ray detector which detects the X-ray irradiation and outputs a detected signal showing a result of the detection; a storage which stores offset information of the X-ray detector; and a reference information generator which generates acquisition reference information for acquiring a start timing of imaging by the imager from the detected signal based on the offset information stored in the storage. Therefore, offset information of the X-ray detector is stored in advance in the storage, so that the operation for adjusting the acquisition reference information according to variation in the offset value of each X-ray detector becomes unnecessary.

Further, an imaging device of the present invention includes an imager which images an X-ray image generated by X-ray irradiation; an X-ray detector which detects the X-ray irradiation and outputs a detected signal showing a result of the detection; and a reference information generator which acquires offset information of the X-ray detector based on the detected signal and generates acquisition reference information for acquiring a start timing of imaging by the imager from the detected signal based on the offset information. Thus, acquisition reference information is generated based on a detected signal from the X-ray detector, and based on this acquisition reference information, an imaging start timing can be acquired from the detected signal, so that regardless of variation in the offset value of the X-ray detector included in the detected signal, the imaging start timing can be accurately acquired each time of X-ray irradiation. Further, the operation for adjusting the acquisition reference information according to variation in the offset value of each X-ray detector becomes unnecessary.

Further, preferably, the reference information generator generates the acquisition reference information based on the offset information and an intensity of the X-ray irradiation. Thus, acquisition reference information is generated based on the offset information and the X-ray irradiation intensity, so that the imaging start timing can be accurately acquired regardless of fluctuation in the X-ray irradiation intensity.

Effect of the Invention

The present invention can provide an imaging device which can accurately generate a trigger showing an X-ray imaging start according to an offset value of the X-ray detector.

DESCRIPTION OF THE REFERENCE NUMERALS

1: X-ray irradiation device, 2, 2a: X-ray imaging device, 3: PC, 3a: Memory, 4: Display, 5: Optical image acquiring part, 6, 6a: Controller, 7: Imager, 8: Connecting part, 9, 9a: Trigger generating unit, 10, 10a: X-ray imaging system, 12: Holding member, 61: Signal processor, 62: Trigger processor, 63: I/O controller, 64, 68: A/D converter, 65: CCD driver, 71: Scintillator, 72: CCD, 73: CCD controller, 81: Connector, 90: X-ray detector, 91: PD, 92: Amplifier, 92a: I-V conversion amplifier, 92b: Gain amplifier, 93, 931: Trigger generator, 93a: EP-ROM, 93b: Comparator, D/A converter 66, L1: signal cable, L11: Detected signal line, L12: Control signal line, L13: Image information line, L2: Signal cable

BEST MODE FOR CARRYING OUT THE INVENTION

Hereinafter, preferred embodiments of the present invention will be described in detail with reference to the drawings.

First Embodiment

Figure 1:
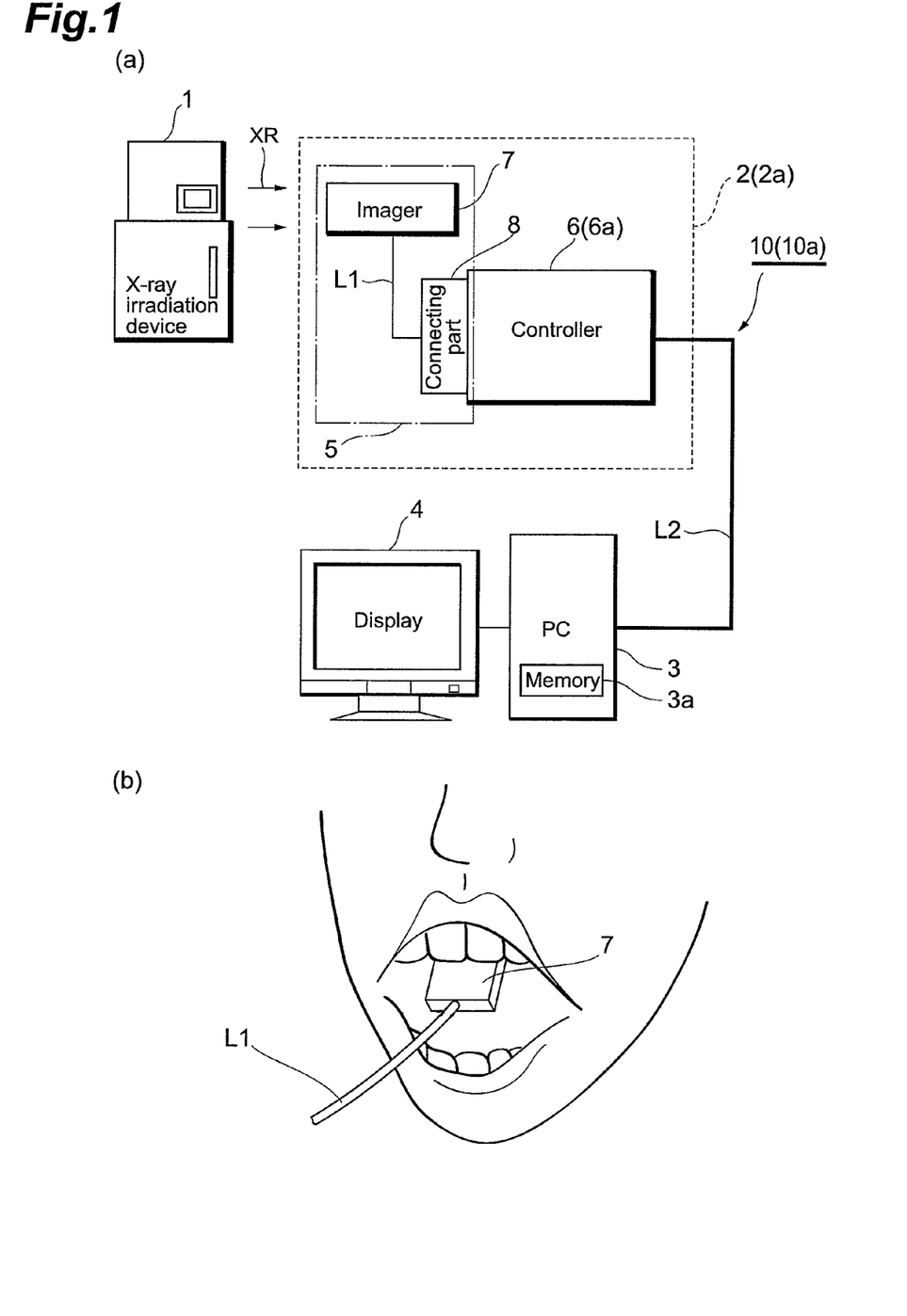
FIG. 1 is a block diagrams showing a configuration of an X-ray imaging system of an embodiment of the present invention.

First, a configuration of an X-ray imaging system 10 will be described with reference to FIG. 1(a). The X-ray imaging system 10 is a medical X-ray imaging system for X-ray imaging teeth, etc., of an examinee. This X-ray imaging system 10 includes an X-ray irradiation device 1, an X-ray imaging device 2, a PC (Personal Computer) 3, and a display 4. The X-ray irradiation device 1 irradiates teeth, etc., with an X-ray, and is configured as a fixed installation type. The X-ray irradiation device 1 performs steady X-ray irradiation (X-ray XR) corresponding to a voltage waveform of a complete DC voltage obtained by using a high-frequency inverter until an input of an X-ray irradiation ending instruction (or until an irradiation ending timer terminates). The X-ray irradiation device 1 can also perform periodic X-ray irradiation (X-ray XR) corresponding to a half-wave rectified waveform of an AC power supply voltage.

The X-ray imaging device 2 is for imaging an X-ray image of teeth, etc., and includes an optical image acquiring part 5 and a controller 6. The optical image acquiring part 5 includes an imager 7 and a connecting part 8, and the imager 7 is connected to the connecting part 8 via a signal cable L1. The imager 7 includes a CCD 72 described later, and images an X-ray image of teeth, etc., by using this CCD 72. The imager 7 has dimensions and a shape capable of being easily inserted into the oral cavity of an examinee. Here, FIG. 1(b) shows an example of a state where the imager 7 is inserted into the oral cavity of an examinee. The imager 7 is inserted to the inside of the front teeth on the upper jaw of the examinee, and from this imager 7, the signal cable L1 extends to the outside of the oral cavity. The controller 6 is connected to the PC 3 via the signal cable L2. The controller 6 controls the optical image acquiring part 5 (specifically, imager 7) and transmits image data to the PC 3 in response to various control instructions transmitted from the PC 3 to the optical image acquiring part 5. The signal cable L2 is a USB (Universal Serial Bus) cable or the like. In addition to transmission and receiving of signals, the USB cable can supply power to the X-ray imaging device 2.

The PC 3 performs various settings (for example, setting of resolution, etc.) and X-ray imaging instruction for the X-ray imaging device 2, various analyses (for example, extraction, enlargement, etc., of a specific region of an image) by loading image data showing an X-ray image from the X-ray imaging device 2, and further, stores data showing the image data and the analysis results in a memory, via the signal cable L2. Further, the PC 3 displays the X-ray image based on the image data loaded from the X-ray imaging device 2 and displays the analysis results, etc., of the image data on the display 4. Here, the display 4 includes a display part such as a CRT (Cathode Ray Tube) or LCD (Liquid Crystal Display).

Figure 2:
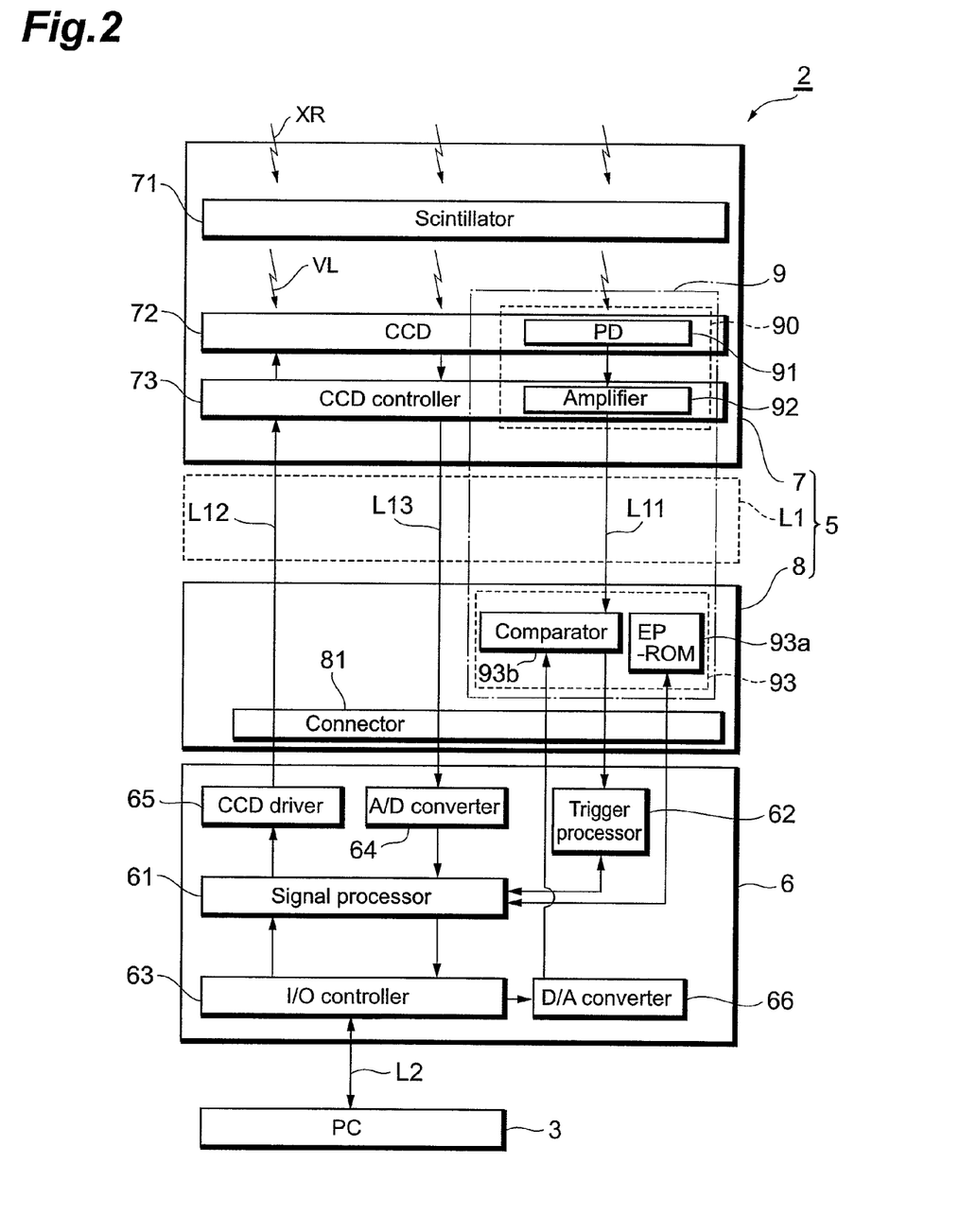
FIG. 2 is a block diagram showing the configuration of the X-ray imaging device of the embodiment of the present invention.

Next, a configuration of the X-ray imaging device 2 will be described with reference to FIG. 2. The imager 7 includes a scintillator 71, a CCD 72, and a CCD controller 73. The signal cable L1 includes a detected signal line L11, a control signal line L12, and an image information line L13. A scintillator 71 emits visible light VL with a light amount corresponding to an energy amount of an X-ray XR when this X-ray XR is made incident thereon. When the CCD 72 is irradiated with the visible light VL from the scintillator 71, the CCD photoelectrically converts this visible light VL to generate a charge corresponding to the light amount of the visible light VL (charge showing an image, hereinafter, referred to as image information), and accumulates this charge in a readable manner (hereinafter, also referred to as imaging). The CCD controller 73 is connected to the CCD 72, the control signal line L12, and the image information line L13. When the CCD controller 73 receives a control signal for the CCD 72 from the controller 6 via the control signal line L12, it controls the driving of the CCD 72 according to this control signal. Here, the control signal for the CCD 72 means an X-ray image imaging instruction and a reading instruction, etc., for reading image information showing an X-ray image. In the description hereinafter, "signal" means an analog signal. The CCD controller 73 reads image information from the CCD 72 based on the control performed by the controller 6, and outputs the read image information to the controller 6 via the image information line L13.

The connecting part 8 is connected to the signal cable L1, and has a function for removably connecting the optical image acquiring part 5 to the controller 6. A control signal for the imager 7 is transmitted to the imager 7 from the controller 6 via the connecting part 8 and the control signal line L12. Image information read from the CCD 72 is transmitted to the controller 6 via the image information line L13 and the connecting part 8. The connecting part 8 includes a connector 81. The connector 81 is, for example, a 36-pin MDR connector, etc.

The optical image acquiring part 5 further includes a trigger generating unit 9. The trigger generating unit 9 generates a trigger signal showing an X-ray image imaging starting instruction or imaging ending instruction, and outputs this trigger signal to the controller 6. The trigger generating unit 9 includes an X-ray detector 90 having a PD 91 (PD: Photo Diode) and an amplifier 92, a detected signal line L11, and a trigger generator 93 which is connected to the X-ray detector 90 via the detected signal line L11. The trigger generator 93 includes an EP-ROM 93a (storage) and a comparator 93b. The X-ray detector 90 is provided in the imager 7. The PD 91 is a monitoring photodiode for monitoring an X-ray XR irradiated by the imager 7, and is provided in the CCD 72. The amplifier 92 is provided in the CCD controller 73. The PD 91 is connected to the amplifier 92, and the amplifier 92 is connected to the detected signal line L11. The detected signal line L11 is included in the signal cable L1. The trigger generator 93 is provided in the connecting part 8.

The controller 6 includes a signal processor 61 (reference information generating part), a trigger processor 62, an I/O controller 63, an A/D converter 64, a CCD driver 65, and a D/A converter 66. The controller 6 has a connection terminal (not shown) to which the connector 81 of the optical image acquiring part 5 is removably attached, and transmits and receives various signals to and from the optical image acquiring part 5 via this connecting terminal. The controller 6 is connected to a signal cable L2, and transmits and receives various data to and from the PC 3 via the signal cable L2. In the following description, "data" means digital data. The signal processor 61 is connected to the trigger processor 62, the I/O controller 63, the A/D converter 64, and the CCD driver 65. Then, the signal processor 61 is connected to the EP-ROM 93a via the connector 81. The signal processor 61 controls the components such as the optical image acquiring part 5 and the trigger processor 62, etc., according to trigger data described later (data showing an X-ray image imaging start timing or imaging end timing) described later input from the trigger processor 62, and command data from the PC 3 input via the I/O controller 63. Alternatively, the signal processor 61 acquires image data from the CCD controller 73 via the A/D converter 64, and transmits this acquired image data to the PC 3 via the I/O controller 63. The signal processor 61 acquires data showing an offset value (offset information) of an output signal (signal S2 described later) output from the X-ray detector 90 from the EP-ROM 93a, and based on the acquired data, generates reference data (acquisition reference information) to be used for trigger signal generation from the trigger generator 93. The signal processor 61 outputs the reference data to the D/A converter 66 via the I/O controller 63. Thereafter, the reference data is converted into an analog signal (reference signal S3) by the D/A converter 66, and this reference signal S3 is output to the comparator 93b. The signal processor 61 may generate the reference signal S3 based on the offset value of the output signal (signal S2) from the X-ray detector 90 and the irradiation intensity of the X-ray XR detected by the X-ray detector 90. The functions of the signal processor 61 may be realized by hardware or software.

Figure 4:
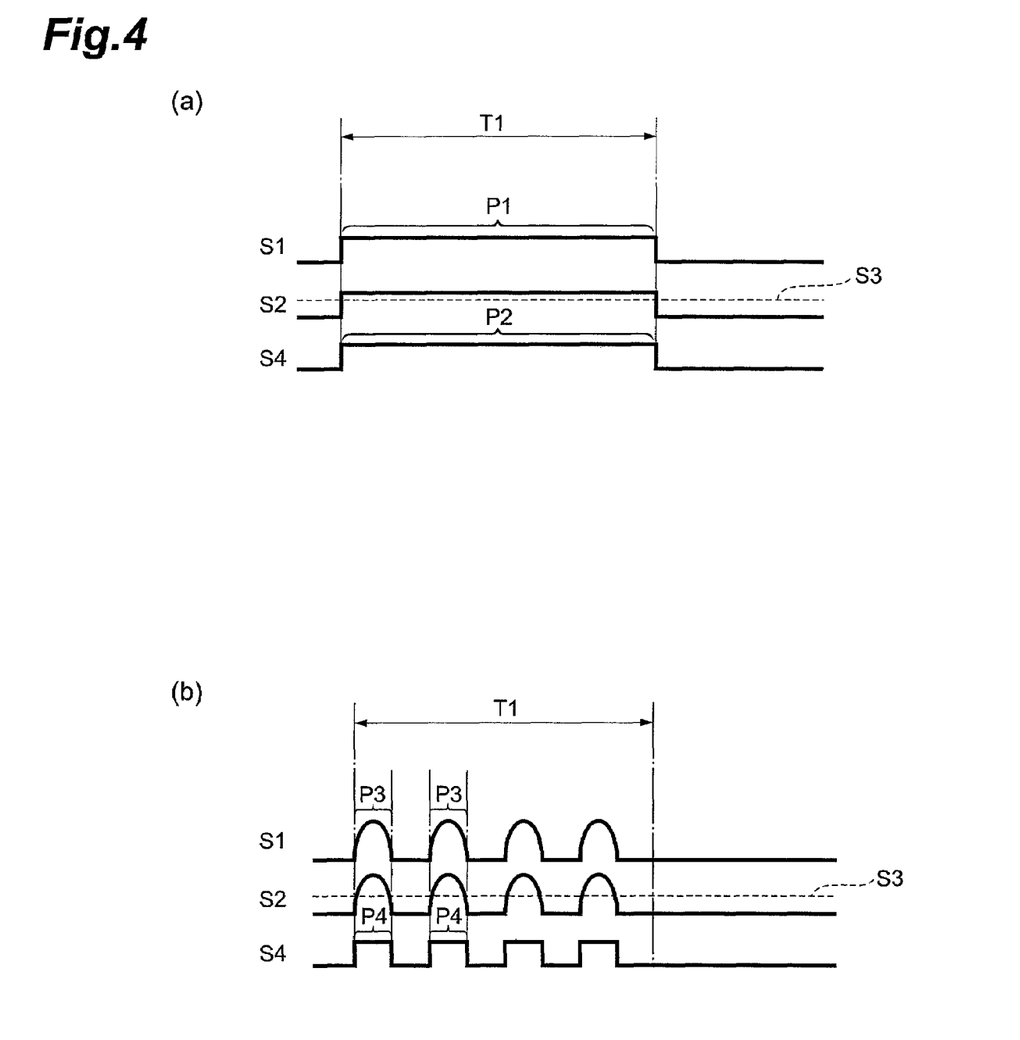
FIG. 4 shows timing charts for describing operations of the trigger generating unit of the embodiment of the present invention.

The trigger processor 62 is connected to the signal processor 61. The trigger processor 62 is connected to the comparator 93b via the connector 81. The trigger processor 62 generates trigger data showing an X-ray image imaging start timing and trigger data showing an imaging end timing according to a pulse (the pulse P2 shown in FIG. 4(a) or the pulse P4 shown in FIG. 4(b)) of the trigger signal S4 input from the comparator 93b via the connector 81, and outputs these trigger data to the signal processor 61. The I/O controller 63 is connected to the signal processor 61 and the signal cable L2. The I/O controller 63 has an interface for transmitting and receiving data to and from the PC 3 via the signal cable L2 based on a data transmission method of USB or the IEEE1394, etc. Without limiting to wired data transmission, the I/O controller 63 may include an interface compliant with the wireless data transmission method of a wireless LAN (Local Area Network) or Bluetooth, etc.

The A/D converter 64 is connected to the signal processor 61. The A/D converter 64 is connected to the CCD controller 73 via the connector 81 and the image signal line L13. The A/D converter 64 converts image information acquired from the CCD controller 73 via the image signal line L13 and the connector 81 into image data, and outputs this image data to the signal processor 61. The CCD driver 65 generates a control signal (signal pulse) according to various control data for the imager 7 input from the signal processor 61, and outputs this control signal to the imager 7. The D/A converter 66 is connected to the I/O controller 63. The D/A converter 66 is connected to the comparator 93b via the connector 81. The D/A converter 66 converts reference data input from the signal processor 61 via the I/O controller 63 into a reference signal S3 of an analog signal, and outputs this reference signal S3 to the comparator 93b via the connector 81.

Figure 3:
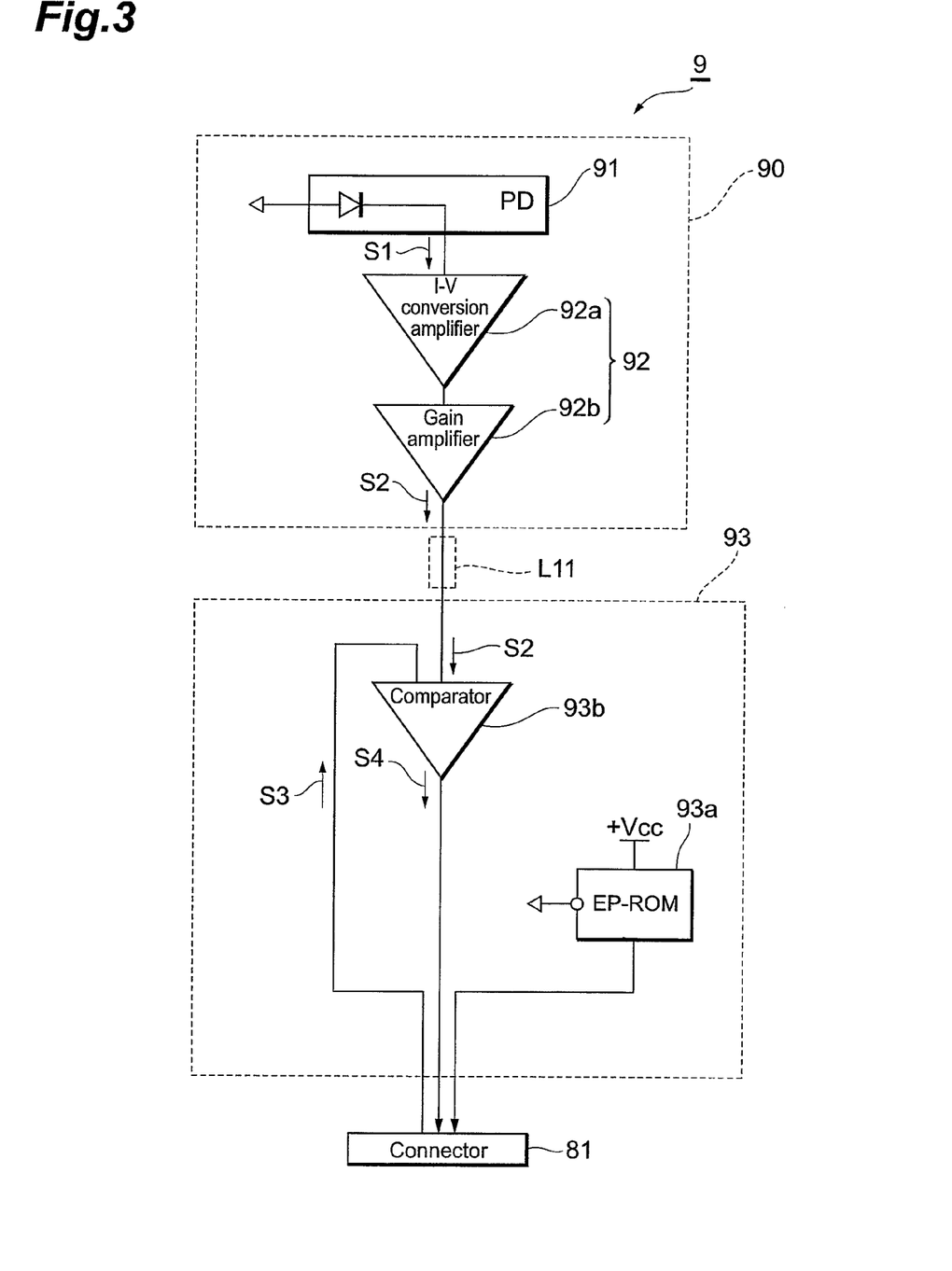
FIG. 3 is a block diagram showing a configuration of a trigger generating unit of the embodiment of the present invention.

Next, with reference to FIG. 3 and FIG. 4, a configuration of the trigger generating unit 9 will be described. The PD 91 detects an X-ray XR irradiated by the X-ray irradiation device 1. The PD 91 outputs an electric signal (hereinafter, referred to as S1) corresponding to the energy amount of the detected X-ray XR. Here, when steady X-ray irradiation corresponding to a voltage waveform of a complete DC voltage is performed by the X-ray irradiation device 1, as shown in FIG. 4(a), the signal S1 includes a pulse P1 with a pulse width corresponding to the entire X-ray irradiation period T1 (approximately, several tens of msec to several seconds). This pulse P1 is a pulse generated by steady X-ray irradiation corresponding to a voltage waveform of a complete DC voltage. When periodic X-ray irradiation corresponding to a half-wave rectified waveform of an AC power supply voltage is performed by the X-ray irradiation device 1, as shown in FIG. 4(b), the signal S1 includes a plurality of periodic pulses P3 in the entire X-ray irradiation period T1. The pulses P3 are generated by periodic X-ray irradiation corresponding to the half-wave rectified waveform of an AC power supply voltage. The amplifier 92 includes an I-V conversion amplifier 92a and a gain amplifier 92b. The I-V conversion amplifier 92a is connected to the PD 91, and converts the signal S1 input from the PD 91 into a voltage value. The gain amplifier 92b is connected to the I-V conversion amplifier 92a, and outputs a signal S2 (detected signal) which is obtained by amplifying the signal S1 converted into a voltage value by the I-V conversion amplifier 92a to a signal level which can be processed by the connecting part 8 on the subsequent stage. The gain amplifier 92b is connected to the detected signal line L11, and outputs the signal S2 to the trigger generator 93 via the detected signal line L11.

The EP-ROM 93a is connected to the connector 81. The EP-ROM 93a is connected to the signal processor 61 via the connector 81, and outputs data showing the offset value of the output signal (signal S2) from the X-ray detector 90 to the signal processor 61 via the connector 81 based on control by the signal processor 61. The EP-ROM 93a stores data such as the model number, the serial number, the manufacturing date, shipment history, etc., of the optical image acquiring part 5 (or the trigger generating unit 9 or the X-ray detector 90), and data showing the offset value of the output signal (signal S2) from the X-ray detector 90 and a plurality of values (values for providing an allowance of the detection sensitivity) near the offset value. The offset value stored in the EP-ROM 93a is an offset value actually measured in advance by using the trigger generating unit 9. A plurality of offset values corresponding to the use environment (for example, temperature) of the optical image acquiring part 5 may be stored in the EP-ROM 93a. In this case, the memory 3a of the PC 3 stores various data showing a correction value for the offset value and the resolution for image reading for each model number and serial number of the optical image acquiring part 5 (or the trigger generating unit 9 or X-ray detector 90) and each use environment (for example, temperature) of the optical image acquiring part 5, and the PC 3 performs various controls of trigger data generation and image reading, etc., by the controller 6 based on the above-described various data stored in the memory 3a.

The comparator 93b is connected to the detected signal line L11 and the connector 81. The comparator 93b is connected to the trigger processor 62 and the D/A converter 66 via the connector 81. The comparator 93b compares the signal S2 input via the detected signal line L11 and the reference signal S3 input via the connector 81 from the D/A converter 66. Then as shown in FIG. 4(a) and FIG. 4(b), the comparator 93b outputs the pulse P2 of the trigger signal S4 when the value of the signal S2 exceeds the value of the reference signal S3. When steady X-ray irradiation corresponding to a voltage waveform of a complete DC voltage is performed by the X-ray irradiation device 1, as shown in FIG. 4(a), the trigger signal S4 includes the pulse P2 with a pulse width substantially corresponding to the entire X-ray irradiation period T1 (pulse width of pulse P1). When periodic X-ray irradiation corresponding to a half-wave rectified waveform of an AC power supply voltage is performed by the X-ray irradiation device 1, as shown in FIG. 4(b), the trigger signal S4 includes a plurality of pulses P4 corresponding to the pulses P3.

Figure 5:
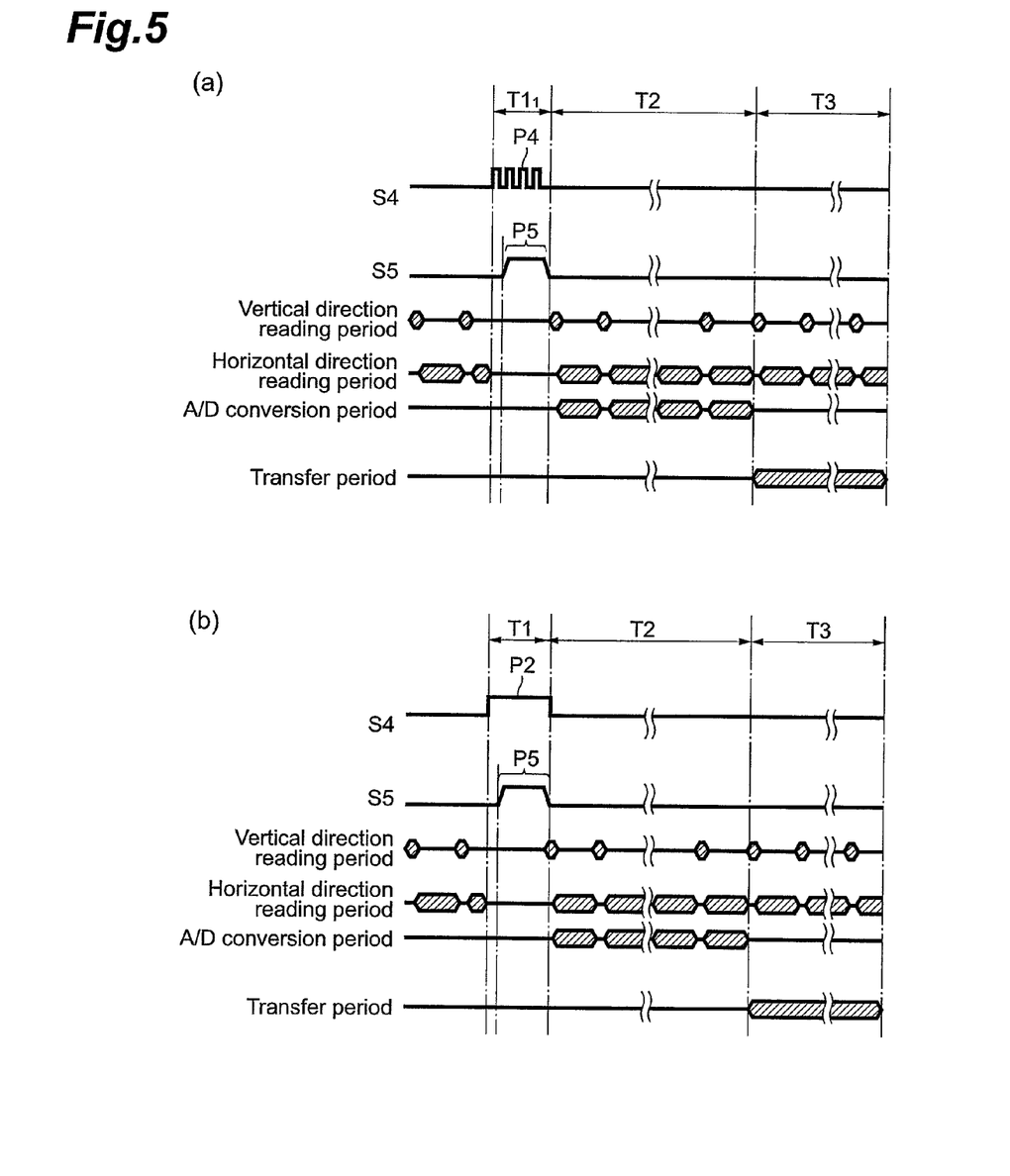
FIG. 5 shows timing charts for describing operations of the X-ray imaging device of the embodiment of the present invention.

Next, operations of the X-ray imaging device 2 will be described with reference to FIG. 5. When the trigger signal S4 is input from the trigger generating unit 9, the trigger processor 62 outputs trigger data showing an X-ray image imaging start timing and trigger data showing an imaging end timing to the signal processor 61 according to this trigger signal S4. In this case, when the trigger processor 62 detects a rise timing of the pulse P2 (or pulse P4), in synchronization with this timing, outputs trigger data showing an imaging start timing to the signal processor 61. Then, in synchronization with a timing at which a predetermined period $T1_1$ (period preset corresponding to the entire X-ray irradiation period T1) has elapsed from the rise timing of the pulse P2 (or pulse P4), the trigger processor 62 outputs trigger data showing an imaging end timing to the signal processor 61 (first imaging mode). The first imaging mode can be applied to both the case where steady X-ray irradiation corresponding to the voltage waveform of a complete DC voltage is performed by the X-ray irradiation device 1 and the case where periodic X-ray irradiation corresponding to the half-wave rectified waveform of an AC power supply voltage is performed by the X-ray irradiation device 1. FIG. 5(a) is a timing chart of the first imaging mode applied for the signal S4 including the pulses P4. When steady X-ray irradiation corresponding to a voltage waveform of a complete DC voltage is performed by the X-ray irradiation device 1, instead of the first imaging mode, as shown in FIG. 5(b), the trigger processor 62 can output trigger data showing an imaging end timing in synchronization with a fall timing of the pulse P2 (second imaging mode).

When steady X-ray irradiation corresponding to a voltage waveform of a complete DC voltage is performed by the X-ray irradiation device 1, the trigger processor 62 is set to either imaging mode of the first imaging mode or the second imaging mode based on command data transmitted via the signal processor 61 from the PC 3. On the other hand, when periodic X-ray irradiation corresponding to a half-wave rectified waveform of an AC power supply voltage is performed by the X-ray irradiation device 1, the trigger processor 62 is set to the first imaging mode. The X-ray imaging device 2 may be configured so that the imaging end timing in the first imaging mode is detected not by the trigger processor 62 but by the signal processor 61. The CCD driver 65 outputs a pulse P5 (control signal S5) with a pulse width corresponding to the imaging period (period $T1_1$ or the entire X-ray irradiation period T1) since trigger data showing an imaging start timing is input into the signal processor 61 until trigger data showing an imaging end timing is input into the signal processor 61 to the imager 7 based on control by the signal processor 61. The imager 7 starts imaging (accumulation of image information) in synchronization with a rise timing of the pulse P5, and ends imaging in synchronization with a fall timing of the pulse P5. Thereafter, the signal processor 61 reads image information accumulated in the imaging period by the imager 7 (period T2). In this case, the CCD controller 73 of the imager 7 alternately reads a horizontal component (horizontal direction) and a vertical component (vertical direction) of image information according to a resolution designated in advance via the PC 3, etc., based on control by the signal processor 61. Image information thus read from the CCD 72 by the CCD controller 73 is successively converted into image data by the A/D converter 64, and the image data is loaded into the signal processor 61. Then, after the period T2, the signal processor 61 transfers the image data loaded from the imager 7 via the A/D converter 64 to the PC 3 via the I/O controller 63 in order (period T3).

As described above, the offset value of the X-ray detector 90 is stored in the EP-ROM 93a, so that the offset value is read from the EP-ROM 93a, and based on this offset value, the reference signal S3 to be used for trigger signal generation is generated. Thus, the offset value is stored in advance in the EP-ROM 93a, so that each time of trigger generation, there is no need to adjust the reference signal S3 to be used for trigger signal generation according to variation in the offset value of each X-ray detector 90. In addition, data such as the model number and the serial number of the optical image acquiring part 5 (or the trigger generating unit 9 or the X-ray detector 90) are stored in the EP-ROM 93a, so that these data are prevented from being falsified or lost. Further, according to the model number and the serial number of the optical image acquiring part 5 (or the trigger generating unit 9 or the X-ray detector 90) stored in the EP-ROM 93a and the use environment (for example, temperature), etc., of the optical image acquiring part 5, etc., correction, etc., of the offset value can be performed easily by software via the PC 3. Therefore, regardless of fluctuations in the use environment of the optical image acquiring part 5, trigger signal generation (acquisition of the imaging start timing) can be reliably performed. Therefore, the convenience is improved and erroneous operation and erroneous detection are suppressed. A plurality of correction values for the offset value can be used, so that the trigger detection sensitivity can be flexibly adjusted. There is no need to use a trimmer resistance which is normally used in the trigger generator 93 to cope with the variation in the offset value of the X-ray detector 90, so that the device configuration of the trigger generator 93 becomes simple, and the cost is reduced. Further, when the reference signal S3 is generated based on the offset value and the irradiation intensity of the X-ray XR detected by the X-ray detector 90, the imaging start timing and the imaging end timing can be reliably acquired regardless of fluctuation in the irradiation intensity of the X-ray XR.

Second Embodiment

Figure 6:
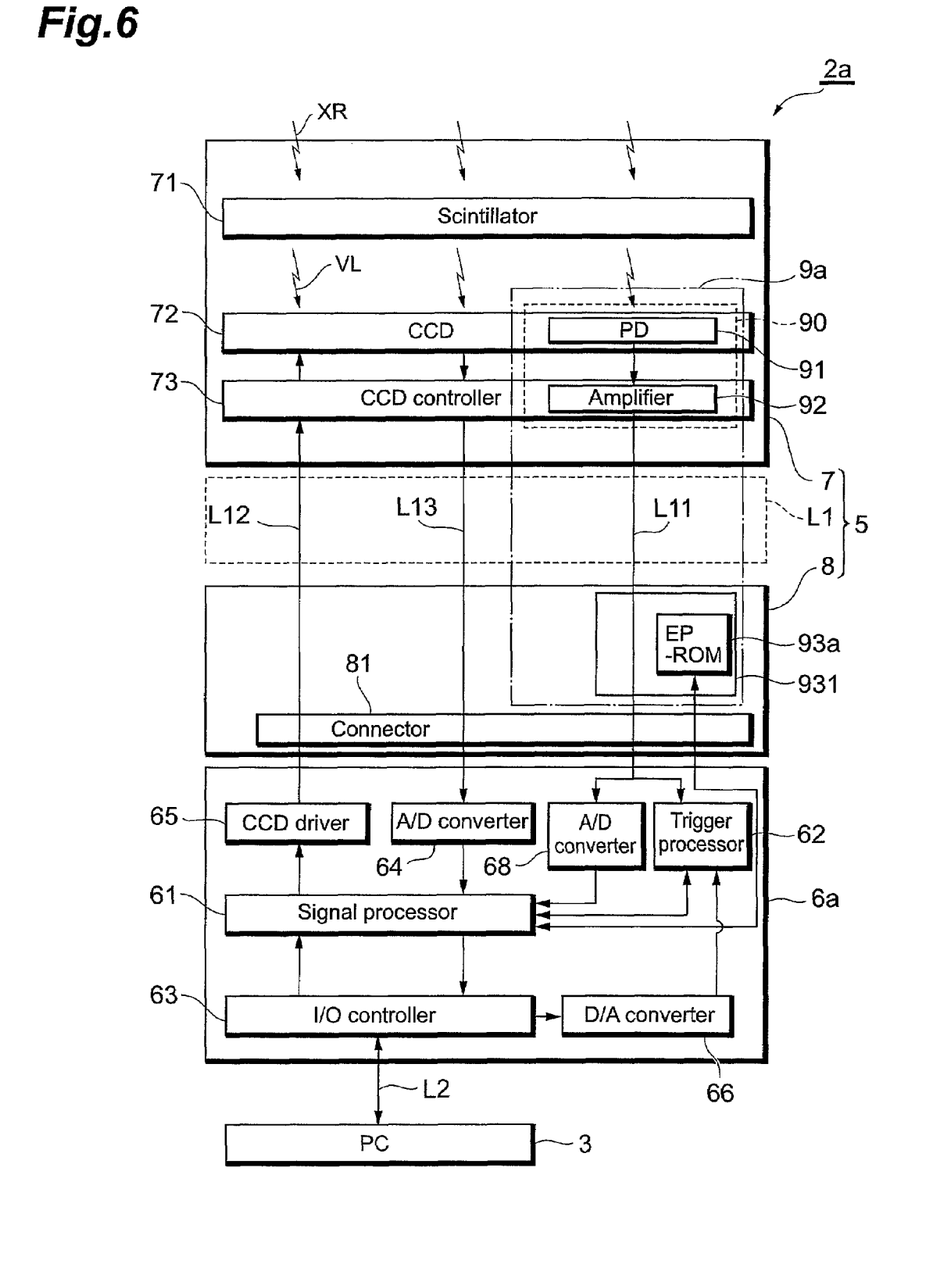
FIG. 6 is a block diagram showing another X-ray imaging device of an embodiment of the present invention.

An X-ray imaging system 10 of a second embodiment includes an X-ray imaging device 2a shown in FIG. 6 instead of the X-ray imaging device 2 of the first embodiment. First, a configuration of the X-ray imaging device 2a is described. The X-ray imaging device 2a includes a controller 6a and a trigger generating unit 9a instead of the controller 6 and the trigger generating unit 9 of the X-ray imaging device 2. The controller 6a further includes an A/D converter 68 in addition to the configuration of the controller 6. The A/D converter 68 is connected to the amplifier 92 via the connector 81, a trigger generator 931, and the signal cable L1. The A/D converter 68 is connected to the signal processor 61. The A/D converter 68 converts a signal S2 input from the amplifier 92 into digital data, and outputs digital data showing this signal S2 to the signal processor 61. The signal processor 61 acquires an offset value of the X-ray detector 90 included in this signal S2 based on digital data showing the signal S2 input from the A/D converter 68, and generates reference data showing a reference value for trigger data generation based on this acquired offset value (or this offset value and an irradiation intensity of the X-ray XR). Then, the signal processor 61 outputs this generated reference data to the D/A converter 66 via the I/O controller 63. The reference data is converted into an analog signal (an analog signal showing a reference value for trigger data generation, corresponding to the reference signal S3 of the first embodiment) by the D/A converter 66, and output to the trigger processor 62. The trigger processor 62 is connected to the amplifier 92 via the connector 81, the trigger generator 931, and the signal cable L1. The trigger processor 62 is connected to the signal processor 61 and the D/A converter 66. The trigger processor 62 of the second embodiment performs the same processing as that of the comparator 93b based on the signal S2 input from the amplifier 92 and the analog signal (analog signal showing a reference value for trigger data generation) input from the D/A converter 66. The A/D converter 68 converts the signal S2 input from the amplifier 92 into digital data, and outputs this digital data to the signal processor 61.

Figure 7:
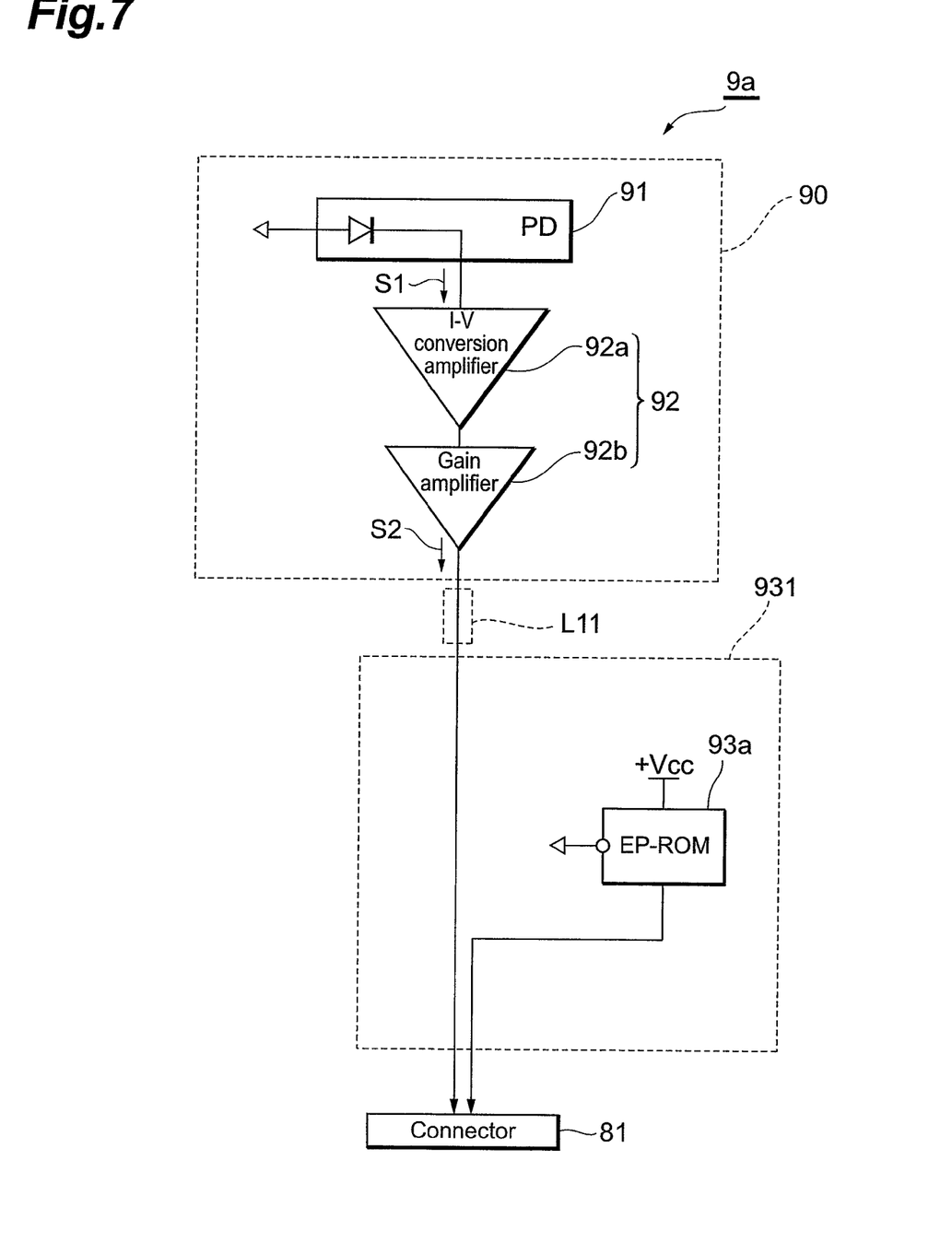
FIG. 7 is a block diagram showing a configuration of another trigger generating unit of an embodiment of the present invention.

The trigger generating unit 9a includes a trigger generator 931 instead of the trigger generator 93 of the trigger generating unit 9 as shown in FIG. 7. The trigger generator 931 includes EP-ROM 93a, however, it does not include the comparator 93b. The signal S2 input from the amplifier 92 is directly output to the trigger processor 62 and the A/D converter 68 via the signal cable L1, the trigger generator 931, and the connector 81. The EP-ROM 93a is connected to the signal processor 61 of the controller 6a via the connector 81. The EP-ROM 93a stores data such as the model number, the serial number, the manufacturing date, and the shipment history of the optical image acquiring part (or the trigger generating unit 9a or the X-ray detector 90). In this case, the memory 3a of the PC 3 stores reference data showing a reference value for trigger data generation and data showing a resolution for image reading for each data showing the model number and the serial number of the optical image acquiring part 5 (or the trigger generating unit 9a and the X-ray detector 90). The PC 3 performs various controls for trigger data generation and image reading, etc., by the X-ray imaging device 2 based on the various data stored in the memory 3a.

Next, operations of the X-ray imaging device 2a of the second embodiment will be described. When the signal S2 is input from the trigger generating unit 9a, the trigger processor 62 generates trigger data showing an X-ray image imaging start timing and trigger data showing an imaging end timing based on the signal S2 and an analog signal (analog signal showing a reference value for trigger data generation) input from the D/A converter 66, and outputs these trigger data to the signal processor 61. The subsequent operations of the X-ray imaging device 2a are described by replacing the signal S4, the pulse P2, and the pulse P4 in the description of the operations of the X-ray imaging device 2 of the first embodiment and FIG. 5 by the signal S2, the pulse P1, and the pulse P3, respectively.

As described above, the X-ray imaging device 2a of the second embodiment generates reference data showing a reference value for trigger data generation based on the signal S2 from the X-ray detector 90. Therefore, preferable reference data for trigger data generation can be generated each time of X-ray imaging. Therefore, the imaging start timing and the imaging end timing can be reliably acquired. The trigger generator 93 does not use the comparator 93b, so that the device configuration of the trigger generator 931 becomes simple, and the cost is reduced. Further, data such as the model number and the serial number of the optical image acquiring part 5 (or the trigger generating unit 9a or the X-ray detector 90) are written on the EP-ROM 93a, so that these data are prevented from being falsified or lost. The reference data for trigger data generation is generated according to the irradiation intensity of the X-ray XR irradiated by the X-ray irradiation device 1, so that the imaging start timing and the imaging end timing can be reliably acquired regardless of fluctuation in the irradiation intensity of the X-ray XR.

Further, the present invention is not limited to the first and second embodiments, and can be variously modified. For example, in place of the trigger generator 93 and the EP-ROM 93a of the trigger generator 931, a writable/readable flash memory can be used. In this case, by using the PC 3, data in the memory can be easily written, rewritten, and deleted. Therefore, data such as the model number and the serial number, the offset value (and the correction value thereof), and the use environment (for example, the temperature) of the optical image acquiring part 5 (or the trigger generating unit 9, the trigger generating unit 9a, and the X-ray detector 90) can be easily updated.

The invention claimed is:

1. An imaging device comprising:
   an imager which images an X-ray image generated by X-ray irradiation;
   an X-ray detector which detects the X-ray irradiation and outputs a detected signal showing a result of detection;
   a storage which stores offset information of the X-ray detector; and
   a reference information generator which generates acquisition reference information for acquiring a start timing of imaging by the imager from the detected signal based on the offset information stored in the storage.

2. An imaging device comprising:
   an imager which images an X-ray image generated by X-ray irradiation;
   an X-ray detector which detects the X-ray irradiation and outputs a detected signal showing a result of detection;
   a reference information generator which acquires offset information of the X-ray detector based on the detected signal and generates acquisition reference information for acquiring a start timing of imaging by the imager from the detected signal based on the offset information.

3. The imaging device according to claim 1, wherein the reference information generator generates the acquisition reference information based on the offset information and an intensity of the X-ray irradiation.

4. The imaging device according to claim 2, wherein the reference information generator generates the acquisition reference information based on the offset information and an intensity of the X-ray irradiation.

* * * * *